(12) United States Patent
Agyare

(10) Patent No.: US 10,045,106 B1
(45) Date of Patent: Aug. 7, 2018

(54) MICROPHONE COVER SYSTEM

(71) Applicant: George Agyare, Boilingbrook, IL (US)

(72) Inventor: George Agyare, Boilingbrook, IL (US)

( * ) Notice: Subject to any disclaimer, the term of this patent is extended or adjusted under 35 U.S.C. 154(b) by 0 days.

(21) Appl. No.: 15/417,403

(22) Filed: Jan. 27, 2017

(51) Int. Cl.
H04R 1/02 (2006.01)
H04R 1/08 (2006.01)
A61L 9/12 (2006.01)
H04R 1/12 (2006.01)
H04M 1/17 (2006.01)

(52) U.S. Cl.
CPC .............. *H04R 1/086* (2013.01); *A61L 9/12* (2013.01); *H04M 1/17* (2013.01); *H04R 1/08* (2013.01); *H04R 1/12* (2013.01); *A61L 2209/13* (2013.01); *H04R 2499/11* (2013.01)

(58) Field of Classification Search
CPC .......... H04R 1/08; H04R 1/083; H04R 1/086; H04R 1/12; H04R 2499/11; H04M 1/17; H04M 1/21; A61L 9/12; A61L 2209/13
USPC .................. 381/122, 355, 359, 360, 361; 379/433.02, 433.11, 432, 437, 439, 451, 379/452
See application file for complete search history.

(56) References Cited

U.S. PATENT DOCUMENTS

| 2,650,269 | A | | 8/1953 | Webb | |
|---|---|---|---|---|---|
| 3,589,106 | A | * | 6/1971 | Onuki | A61L 9/01 379/452 |
| 4,953,703 | A | | 9/1990 | Virginio | |
| 5,054,063 | A | * | 10/1991 | Lo | H04R 1/12 379/439 |
| 5,136,640 | A | * | 8/1992 | Kim | H04M 1/21 379/439 |
| 6,071,527 | A | | 6/2000 | Tsujino et al. | |
| D588,583 | S | | 3/2009 | McDougal | |
| 2003/0219116 | A1 | * | 11/2003 | Hudgins | H04M 1/17 379/433.11 |
| 2004/0052395 | A1 | | 3/2004 | Sin | |
| 2007/0098148 | A1 | * | 5/2007 | Sherman | H04M 1/21 379/452 |
| 2012/0076327 | A1 | | 3/2012 | Benn et al. | |

* cited by examiner

Primary Examiner — Huyen D Le

(57) ABSTRACT

A microphone cover system for includes a microphone to capture audible sounds. An odor enhancing unit is removably positioned on the microphone to inhibit moisture from contacting the microphone. The odor enhancing unit is comprised of a fluid permeable material to facilitate sound waves to pass therethrough to the microphone. Moreover, the odor enhancing unit emits a selected odor to enhance an odor associated with the microphone.

1 Claim, 3 Drawing Sheets

MICROPHONE COVER SYSTEM

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to microphone devices and more particularly pertains to a new microphone device for enhancing an odor associated with a microphone.

BRIEF SUMMARY OF THE INVENTION

An embodiment of the disclosure meets the needs presented above by generally comprising a microphone to capture audible sounds. An odor enhancing unit is removably positioned on the microphone to inhibit moisture from contacting the microphone. The odor enhancing unit is comprised of a fluid permeable material to facilitate sound waves to pass therethrough to the microphone. Moreover, the odor enhancing unit emits a selected odor to enhance an odor associated with the microphone.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
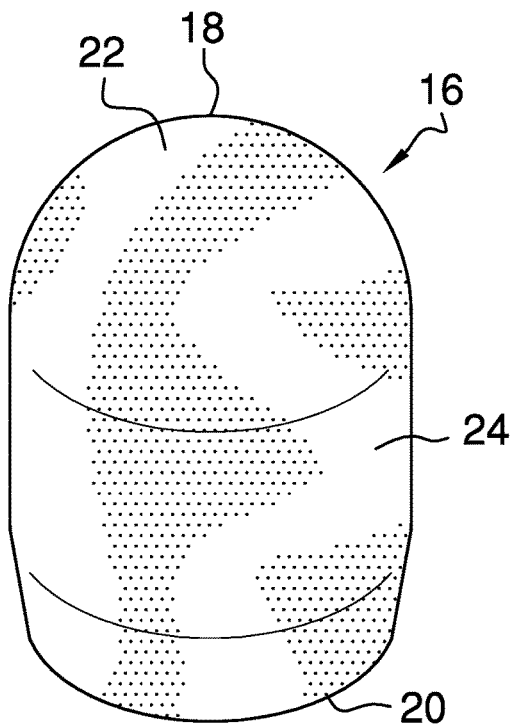
FIG. 1 is a front perspective view of a cover of a microphone cover system according to an embodiment of the disclosure.
Figure 2:
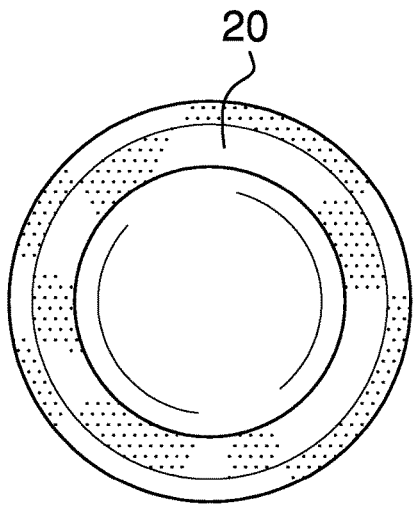
FIG. 2 is a bottom view of a cover of an embodiment of the disclosure.
Figure 3:
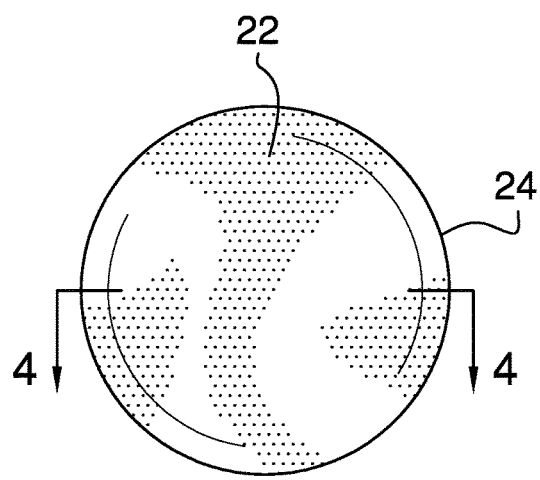
FIG. 3 is a top view of a cover of an embodiment of the disclosure.
Figure 4:
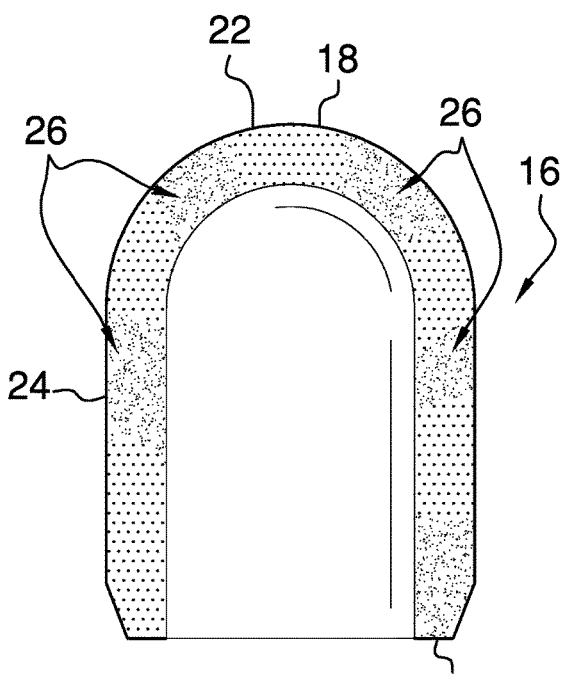
FIG. 4 is a cross sectional view of a cover of an embodiment of the disclosure.
Figure 5:
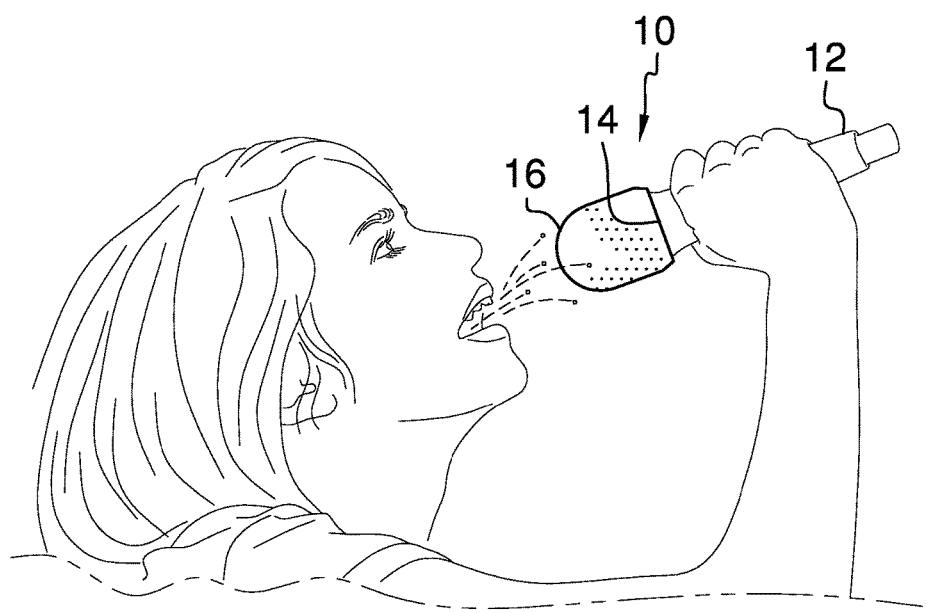
FIG. 5 is a perspective in-use view of an embodiment of the disclosure.

With reference now to the drawings, and in particular to FIGS. 1 through 5 thereof, a new microphone device embodying the principles and concepts of an embodiment of the disclosure and generally designated by the reference numeral 10 will be described.

As best illustrated in FIGS. 1 through 5, the microphone cover system 10 generally comprises a microphone 12 that has a first end 14 and the first end 14 captures audible sounds. The microphone 12 may be a condenser microphone, a dynamic microphone or any other conventional type of microphone 12 typically employed in live performance and studio performance.

An odor enhancing unit 16 is provided and the odor enhancing unit 16 is removably positioned on the microphone 12. The odor enhancing unit 16 inhibits moisture from contacting the microphone 12. Moreover, the odor enhancing unit 16 is comprised of a fluid permeable material to facilitate sound waves to pass to the microphone 12. The fluid permeable material may be expanded foam, a textile or any other material commonly used in microphone 12 filtering. The odor enhancing unit 16 emits a selected odor. In this way the odor enhancing unit 16 enhances an odor associated with the microphone 12.

The odor enhancing unit 16 comprises a cover 18 that has a primary end 20, a secondary end 22 and an outer wall 24 extending therebetween. The outer wall 24 is continuous such that the cover 18 has a cylindrical shape. The primary end 20 is open to insertably receive the first end 14 of the microphone 12 having the outer wall 24 extending downwardly along the microphone 12. The secondary end 22 is rounded and the cover 18 is comprised of the fluid permeable material.

A chemical scent 26 is provided and the chemical scent 26 is infused into the outer wall 24 of the cover 18. The chemical scent 26 comprises a volatile liquid that readily vaporizes at room temperature. Thus, the chemical scent 26 emits a selected olfactory odor that can be detected by a person. The selected olfactory odor may be jasmine, lavender, mint or any other pleasing olfactory odor. In this way the chemical scent 26 enhances an olfactory odor associated with the microphone 12. Additionally, the chemical scent 26 comprises a tasteless material.

In use, the cover 18 is positioned on the microphone 12 and the microphone 12 is manipulated in the convention of live performance and studio performance. The cover 18 inhibits saliva and other moisture from contacting the microphone 12. In this way the cover 18 inhibits bacterial growth on the microphone 12 that can emit an unpleasant olfactory odor. Moreover, the chemical scent 26 emits the selected olfactory odor to enhance the odor associated with the microphone 12. The cover 18 is replaced when the chemical scent 26 is exhausted.

With respect to the above description then, it is to be realized that the optimum dimensional relationships for the parts of an embodiment enabled by the disclosure, to include variations in size, materials, shape, form, function and manner of operation, system and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A microphone cover system being configured to inhibit foul odors from emanating from a microphone, said system comprising:

a microphone having a first end, said first end being configured to capture audible sounds, said first end having a hemispherical end portion and a cylindrical portion extending from said end portion towards a grip coupled to and extending from said first end of said microphone; and an odor enhancing unit being removably positioned on said microphone wherein said odor enhancing unit is configured to inhibit moisture from contacting said microphone, said odor enhancing unit being comprised of a fluid permeable material wherein said odor enhancing unit is configured to facilitate sound waves to pass therethrough to said microphone, said odor enhancing unit emitting a selected odor wherein said odor enhancing unit is configured to enhance an odor associated with said microphone, said odor enhancing unit comprising:

a cover having a primary end, a secondary end and an outer wall extending therebetween, said outer wall being continuous such that said cover has a cylindrical shape, said primary end being open to insertably receive said first end of said microphone having said outer wall extending downwardly along said microphone, said secondary end being rounded wherein said outer wall is complementary in shape to said first end of said microphone, a bottom portion of said outer wall adjacent to said primary end tapering providing an angled surface extending around said primary end wherein said angled surface is configured for facilitating grasping of said cover for removal from said first end of said microphone, and a chemical scent being infused into said outer wall of said cover wherein said chemical scent is configured to enhance an odor associated with said microphone.

\* \* \* \* \*